(12) United States Patent
Checot et al.

(10) Patent No.: US 8,236,353 B2
(45) Date of Patent: Aug. 7, 2012

(54) SELF-PRECIPITATING PHARMACEUTICAL FORMULATIONS FOR THE MODIFIED RELEASE OF AN ACTIVE PRINCIPLE

(75) Inventors: Frédéric Checot, Lyons (FR); Cecile Bonnet-Gonnet, Lyons (FR); You-Ping Chan, Ternay (FR); Olivier Breyne, Lyons (FR); Remi Meyrueix, Lyons (FR)

(73) Assignee: Flamel Technologies (FR)

( * ) Notice: Subject to any disclaimer, the term of this patent is extended or adjusted under 35 U.S.C. 154(b) by 959 days.

(21) Appl. No.: 12/149,541

(22) Filed: May 5, 2008

(65) Prior Publication Data
US 2009/0011028 A1    Jan. 8, 2009

Related U.S. Application Data

(60) Provisional application No. 60/924,216, filed on May 3, 2007.

(30) Foreign Application Priority Data

May 3, 2007    (FR) ...................................... 07 03186

(51) Int. Cl.
*A61K 9/14*    (2006.01)
*A61K 9/64*    (2006.01)
*A61K 9/58*    (2006.01)
*A61K 38/00*   (2006.01)
*A61K 9/52*    (2006.01)

(52) U.S. Cl. ........... 424/489; 514/1.1; 514/12; 424/457; 424/460; 424/462

(58) Field of Classification Search ........................ None
See application file for complete search history.

(56) References Cited

U.S. PATENT DOCUMENTS

| 6,143,314 | A | 11/2000 | Chandrashekar et al. |
| 6,201,072 | B1 | 3/2001 | Rathi et al. |
| 6,630,171 | B1 | 10/2003 | Huille et al. |
| 7,683,024 | B2 * | 3/2010 | Chan et al. .................. 514/19.3 |

(Continued)

FOREIGN PATENT DOCUMENTS

EP    0963758 A2 * 12/1999

(Continued)

OTHER PUBLICATIONS

Fuller, W. et al., "A Procedure for the Facile Synthesis of Amino-Acid N-Carboxyanhydrides," 1976, *Biopolymers*, 15:1869-71.

(Continued)

*Primary Examiner* — Lakshmi Channavajjala
(74) *Attorney, Agent, or Firm* — Patton Boggs LLP

(57) ABSTRACT

The present invention relates to pharmaceutical formulations for the release of an active principle (AP) over a sustained period of time. The invention relates to a liquid formulation comprising at least one active principle (AP) and an aqueous suspension based on colloidal particles of a polymer (PO), wherein said formulation satisfies the following four conditions: (a) the PO is a polyamino acid comprising glutamic residues, wherein some glutamic residues each carry a pendant cationic group (CG), said CG being identical or different from one another, and other glutamic residues each carry a pendent hydrophobic group (GH), said GH being identical or different from one another, (b) the pHf value of the pH of said formulation is between 3.0 and 6.5; (c) at the pHf value, the PO forms a colloidal solution which associates spontaneously and noncovalently with the AP; (d) 1 ml of said formulation precipitates during mixing with a volume of 1 ml of a test buffer solution Tp.

14 Claims, 1 Drawing Sheet

U.S. PATENT DOCUMENTS

| | | | |
|---|---|---|---|
| 7,919,572 B2 * | 4/2011 | Angot et al. | 528/328 |
| 2006/0099264 A1 | 5/2006 | Chan et al. | |
| 2007/0196497 A1 | 8/2007 | Pouliquen et al. | |
| 2007/0248686 A1 | 10/2007 | Touraud et al. | |
| 2009/0012028 A1 | 1/2009 | Chan et al. | |

FOREIGN PATENT DOCUMENTS

| | | |
|---|---|---|
| FR | 2 786 098 | 5/2000 |
| FR | 2 801 226 | 5/2001 |
| FR | 2 881 140 | 7/2006 |
| FR | 2007/0003185 | 5/2007 |
| FR | 2 915 748 | 11/2008 |
| WO | WO 99/18142 | 4/1999 |
| WO | WO 2005/051416 | 6/2005 |
| WO | WO 2007/051923 | 5/2007 |

OTHER PUBLICATIONS

Heeswijk et al., "The Synthesis and Characterization of Polypeptide-Adriamycin Conjugates and its Complexes with Adriamycin, Part I," *Journal of Controlled Release*, 1995; 1:301-315.

* cited by examiner

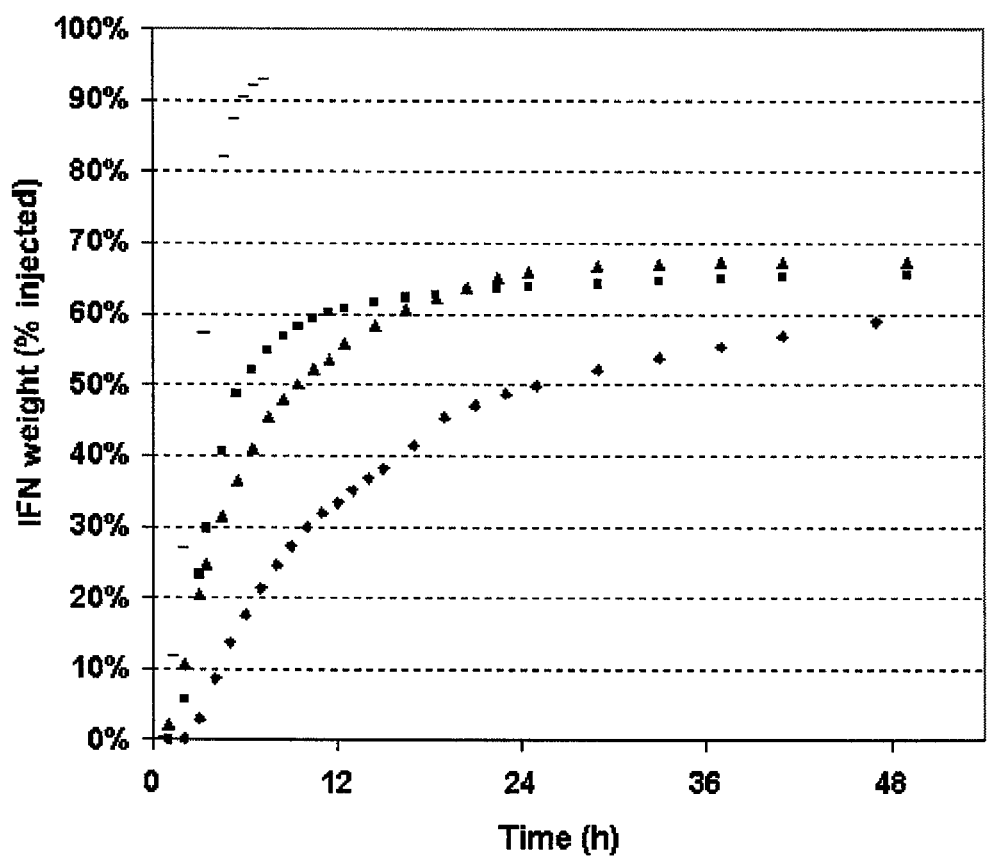

SELF-PRECIPITATING PHARMACEUTICAL FORMULATIONS FOR THE MODIFIED RELEASE OF AN ACTIVE PRINCIPLE

CROSS-REFERENCE TO RELATED APPLICATIONS

This application claims priority to French Application No. 0703186, filed May 3, 2007, currently pending, and U.S. Provisional Application No. 60/924,216, filed May 3, 2007. The contents of which are incorporated herein in their entirety.

FIELD OF THE INVENTION

The present invention relates to novel pharmaceutical formulations for the sustained release of active principle(s) (AP), in particular protein and peptide active principle(s). The patent application also relates to the application or use, in particular therapeutic application or use, of these pharmaceutical formulations. These active pharmaceutical formulations relate both to human therapeutics and veterinary therapeutics.

The reference AP used throughout the present document refers to at least one active principle.

STATE OF THE ART

In the field of the sustained release of pharmaceutical APs, in particular therapeutic peptides/proteins, the aim is very often to reproduce, as best as possible, in the patient a peptide or protein plasma concentration close to the value observed in healthy subject s.

This objective conflicts with the short lifetime of proteins in the plasma, which leads to repeated injections of the therapeutic protein. Consequently, the plasma concentration of a therapeutic protein exhibits a profile characterized by high concentration peaks and very low concentration minima. The concentration peaks, which are much higher than the basal concentration found in a healthy subject, have significant harmful effects to the high toxicity of therapeutic proteins such as certain cytokines. Furthermore, the concentration minima are below the concentration necessary to have a therapeutic effect, which results in poor therapeutic coverage of the patient and serious long-term side effects.

Consequently, in order to reproduce in a patient a plasma concentration of therapeutic protein close to the ideal value for treatment, it is important for the pharmaceutical formulation to allow the release of the therapeutic protein over a sustained period of time, so as to limit variations in plasma concentration over time.

Furthermore, this active formulation should preferably satisfy the following requirements, already known to a person skilled in the art:
1—sustained release of an active and nondenatured therapeutic protein, for example a human or synthetic protein, so that the plasma concentration is maintained at the therapeutic level;
2—sufficiently low viscosity at injection to be easily injectable;
3—biocompatible and biodegradable form exhibiting an excellent toxicity and tolerance profile.

In an attempt to achieve these objectives, one of the best approaches provided in the prior art was to develop sustained-release forms of therapeutic protein(s) composed of relatively nonviscous liquid suspensions of nanoparticles loaded with therapeutic proteins. These suspensions allow easy administration of native therapeutic proteins.

Thus, Flamel Technologies has provided a route in which the therapeutic protein is associated with nanoparticles of a copolyamino acid comprising hydrophobic groups and hydrophilic groups.

Patent application US 2006/0099264 discloses amphiphilic polyamino acids comprising aspartic residues and/or glutamic residues, wherein at least a portion of these residues carry grafts comprising at least one α-tocopherol residue, e.g.: (polyglutamate or polyaspartate grafted with α-tocopherol of synthetic or natural origin). These "hydrophobic modified" homopolyamino acids spontaneously form, in water, a colloïdal suspension of nanoparticles which are capable of readily associate with at least one active protein (insulin) in aqueous suspension at pH 7.4.

The in vivo release duration of the active protein(s) (e.g. insulin) "vectorized" by the suspensions described in US 2006/0099264 would benefit from being extended.

An increase in release duration was partially obtained using the pharmaceutical forms described in PCT application WO-A-05/051416. This application discloses a colloïdal suspension of nanoparticles (0.001-0.5 µm) of hydrophobic modified poly(sodium L-glutamate) injected at a concentration such that, after subcutaneous injection, a gel is formed in situ in the patient on contact with endogenous albumin. The protein is then slowly released over a typical period of one week. However, when the concentration of therapeutic protein to be administered is relatively high, as is the case, for example, for human growth hormone, the release duration is limited to a few days.

The release duration of these forms would benefit from being further extended.

Another route also proposed for prolonging the in vivo release duration of AP after subcutaneous injection is to use a formulation which is liquid at the injection temperature but which forms a gel when the temperature rises to 37° C.

PCT applications WO-A-99/18142 and WO-A-00/18821 relate to aqueous solutions of AP comprising polymers in a dissolved or colloïdal form which can be administered to warm-blooded animals, in particular by injection, and which form a gelled deposit in vivo since the physiological temperature is higher than their gelling temperature. The gel thus formed releases the AP in a sustained fashion. These specific biodegradable polymers are ABA or BAB triblocks with A=polylactic-co-glycolic (PLAGA) or polylactic (PLA) and B=PolyEthylene Glycol. The temperatures for the liquid ⇒gel transformation of these triblock polymers are, for example, 36, 34, 30 and 26° C. Similar polymers (A) described in U.S. Pat. No. 6,143,314, the hydrolysis of these ABA or BAB triblock polymers in vivo results in acids which may not be well tolerated locally.

Patent application PCT/FR2006/002443, by the Applicant, describes polyglutamates modified by histidine derivatives and hydrophobic groups and their applications.

In particular, this application discloses that these polymers are soluble at acidic pH and precipitate at neutral pH. They allow the preparation of formulations for the release of an active principle, such as a therapeutic protein.

In the context of the development of a self-precipitating aqueous liquid formulations for sustained release using such polymers, it has unexpectedly been found that a formulation fulfilling the demanding requirements can only be obtained under certain specific conditions.

For example, the polymer pGluHisOEt α-tocopherol described in the application PCT/FR2006/002443, formulated at pH 5.5 and comprising 45 mg/ml of polymer, does not lead to the expected result.

Lengthy studies by the Applicant have led to the identification of i) formulations comprising cationic polymers (PO) which fulfill the requirements of a self-precipitating system and ii) specific conditions for selecting such formulations. These polymers (PO) can be selected either from polymers described in application PCT/FR2006/002443, or from a novel family of polymers comprising cationic groups and carrying hydrophobic groups.

BRIEF DESCRIPTION OF THE INVENTION

One of the objectives of the invention is to provide novel formulations based on polyglutamate polymers that are modified by cationic amino acid derivatives carrying hydrophobic side groups, are loaded with an active principle (AP) and release the active principle (AP) over a sustained period of several days, or even several weeks.

Another objective of the invention is to provide novel liquid formulations based on polyglutamate polymers modified by cationic amino acid derivatives which carry hydrophobic side groups, the formulations being loaded with an active principle (AP), wherein the composition and concentration of the formulations allow the release duration of an active principle to be optimized for subcutaneous administration.

Another objective of the invention is to provide novel liquid formulations based on polyglutamate polymers modified by cationic amino acid derivatives which carry hydrophobic side groups, the formulations being loaded with an active principle, wherein the formulations composition is such that it allows release of the active principle (AP) over several days, or even several weeks, with the lowest possible concentration of polymer.

Another objective of the invention is to provide novel liquid formulations based on polyglutamate polymers modified by cationic amino acid derivatives which carry hydrophobic side groups, the formulations being loaded with an active principle (AP), wherein the composition and concentration of the formulations allow easy injection through a needle of small size.

Another objective of the invention is to provide novel liquid formulations based on polyglutamate polymers modified by cationic amino acid derivatives which carry hydrophobic side groups which are stable in aqueous solution.

Another objective of the invention is to provide novel formulations based on polyglutamate polymers modified by cationic amino acid derivatives which carry hydrophobic side groups which can be stored in lyophilized form.

Another objective of the invention is to provide novel formulations based on polyglutamate polymers modified by cationic amino acid derivatives which carry hydrophobic side groups which can be easily redispersed after lyophilization.

Another objective of the invention is to provide novel formulations based on polyglutamate polymers modified by cationic amino acid derivatives which carry hydrophobic side groups, the formulations being loaded with active principle (AP), wherein the formulations are stable in lyophilized form.

Another objective of the invention is to provide novel formulations based on polyglutamate polymers modified by cationic amino acid derivatives which carry hydrophobic side groups, wherein the formulations release a protein without affecting its biological activity.

Another objective of the invention is to provide a solid pharmaceutical formulation for the sustained release of active principle (AP), in particular a dry powder form, for example for inhalation and pulmonary administration.

Another objective of the invention is to provide a novel process for the preparation of a formulation for the sustained release of at least one active principle (AP), this formulation being in particular one of the formulations described above.

Another objective of the invention is to provide a novel process for the preparation of medicaments employing these pharmaceutical formulations.

After lengthy and extensive research, the Applicant has found that formulations based on polyglutamate polymers modified by cationic amino acid derivatives which carry hydrophobic side groups optimize the sustained release of therapeutic proteins and peptides.

Accordingly, the present invention first of all relates to an aqueous pharmaceutical formulation for the sustained release of at least one active principle (AP) which can be easily injected, for example via the parenteral route, and which comprises at least one active principle (AP) and an aqueous suspension based on colloïdal particles of a polymer (PO), or of a pharmaceutically acceptable salt thereof, wherein said formulation satisfies the following four conditions:
(a) the polymer (PO) is a polyamino acid comprising glutamic residues, wherein
  some glutamic residues each carry a pendant cationic group (CG), said cationic groups being identical or different from one another,
  other glutamic residues each carry a pendant hydrophobic group (GH), said hydrophobic groups (GH) being identical or different from one another,
  optionally, still other glutamic residues each carry a pendant neutral group (NG), the neutral groups (NG) being identical or different from one another, and
  optionally, yet other glutamic residues are unmodified;
(b) the pH value of said formulation (pHf) is between 3.0 and 6.5;
(c) at pHf, the polymer (PO) forms a colloïdal solution which associates spontaneously and noncovalently with the active principle (AP);
(d) 1 ml of said formulation precipitates during mixing with a volume of 1 ml of a test buffer solution Tp.

Preferably, such a formulation exhibits a precipitation factor PF of greater than 200, preferably of greater than 400, preferably of greater than 800 and more preferably still of greater than 1500.

The invention also relates to an aqueous liquid pharmaceutical formulation for the sustained release of at least one active principle (AP) which can be easily injected, for example via the parenteral route, and which comprises at least one active principle (AP) and an aqueous suspension based on colloïdal particles of a polymer (PO), or a pharmaceutically acceptable salt thereof, which formulation satisfies the following four conditions:
(a) the polymer (PO) is a polyamino acid comprising glutamic residues, wherein
  some glutamic residues each carry a pendant cationic group (CG), said cationic groups being identical or different from one another,
  other glutamic residues each carry a pendant hydrophobic group (GH), said hydrophobic groups (GH) being identical or different from one another,
  optionally, still other glutamic residues each carry a pendant neutral group (NG), the neutral groups (NG) being identical or different from one another, and
  optionally, yet other glutamic residues are unmodified;
(b) the pH value of said formulation (pHf) is between 3.0 and 6.5;
(c) at pHf, the polymer (PO) forms a colloïdal solution which associates spontaneously and noncovalently with the active principle (AP);

(d) said formulation exhibits a precipitation factor PF of greater than 200, preferably of greater than 400, preferably of greater than 800 and more preferably still of greater than 1500.

Moreover, this formulation preferably exhibits a retention factor RQ of greater than 5, preferably of greater than 10, and preferably of greater than 15, and more preferably still of greater than 20.

It has been shown that, for a given concentration of polymer, the kinetics of release of an active principle (AP) depend to a significant extent on the composition of the polymer, i.e. on the respective molar fractions of cationic groups, hydrophobic side grafts and optionally of neutral groups and glutamate groups.

The invention also relates to a process for the preparation of formulations for the sustained release of at least one active principle (AP), these formulations being in particular those described above, the process comprising the following steps:

1) preparing, at a pH value of between 3 and 6.5, an aqueous colloïdal solution of a polyamino acid polymer (PO) comprising glutamic residues, wherein
   some glutamic residues each carry a pendant cationic group (CG), said cationic groups being identical or different from one another,
   other glutamic residues each carry a pendant hydrophobic group (GH), said hydrophobic groups (GH) being identical or different from one another,
   optionally, still other glutamic residues each carry a pendant neutral group (NG), the neutral groups (NG) being identical or different from one another, and
   optionally, yet other glutamic residues are unmodified;
   the respective molar fractions of cationic groups (CG), hydrophobic groups (GH), optionally neutral groups (NG) and optionally glutamate being such that 1 ml of said formulation precipitates during mixing with a volume of 1 ml of a test buffer solution Tp; and
2) adding at least one active principle (AP) to the polymer (PO) obtained in step 1, wherein said active principle noncovalently associates with particles of the colloïdal solution of said polymer, and wherein the step of adding the active principle may be carried immediately prior to the final therapeutic use of the formulation (for example, 30 minutes before).

The invention also relates to a process for the preparation of medicaments, in particular for parenteral, mucosal, subcutaneous, intramuscular, intradermal, transdermal, intraperitoneal or intracerebral administration or administration into a tumor, or even administration by the oral, nasal, pulmonary, vaginal or ocular route, said process consisting essentially in employing at least one formulation as described herein.

DETAILED DESCRIPTION OF THE INVENTION

Definitions

In the present description, the term "cationic group" is understood to mean a group covalently linked to a glutamic residue comprising one or more amino groups or one or more quaternary ammoniums. In cases of an amino functional group, the group will be mainly ionized at any pH below its pKa; in cases of a quaternary ammonium, the group will be ionized at any pH. Unless otherwise specified, alkyl radicals exhibit 1 to 10 carbon atoms.

In the present description, the term "neutral group" is understood to mean a group not carrying a charge at any pH between 3 and 10, and include, for example, groups obtained by condensation on the carboxyl group of a glutamic residue, of ethanolamine, of an alkylene glycol or of a polyalkylene glycol.

The term "pharmaceutically acceptable salts" of the polymer according to the invention, is understood to encompass all the polymers with counterions associated with ionized functions of the polymer.

In the present description, the term "solution" is understood to mean a homogeneous solution of solvent and polymer in the form of individual chains.

In the present description, the term "colloïdal solution" is understood to mean a suspension of particles, the mean diameter of which, measured by the T' test, is less than or equal to 0.5 μm.

In the present description, the term "easily injectable formulation" (for example, by the parenteral route) is understood to mean a formulation exhibiting a dynamic viscosity at 20° C. of less than or equal to 1000 mPa·s. Preferably, the dynamic viscosity of the formulation, measured at 20° C., for a shear gradient of $1000\ s^{-1}$, is preferably less than or equal to 500 mPa·s., preferably of between 2 and 200 mPa·s, for example of between 1.0 and 100 mPa·s, indeed even between 1.0 and 50 mPa·s.

In the present description, the term "small molecule" is understood to mean molecule whose molecular weight is less that 1 kDa, in particular a non proteinic molecule.

In the present description, the term "pHf" is understood to mean the pH of a formulation according to the invention.

In the present description, the term "pH*" is understood to mean the pH of precipitation of a formulation based on polymer PO determined using the P test:

P Test for Measuring the pH for Precipitation pH* by Measuring the Absorbance at 500 nm:

A concentrated solution of polymer PO at 1 or 2 mg/ml and comprising 0.15 M of sodium chloride is brought to pH 4 by addition of acetic acid or of 1 M sodium hydroxide solution and is left stirring for 24 h. This solution is subsequently filtered through a 0.8-0.2 μm filter. This solution is then titrated with a 0.1 M sodium hydroxide solution, the change in absorbance at 500 nm of the solution of polymer PO being recorded as a function of the pH of said solution using a device of the Perkin-Elmer Lambda 35 UV Spectrometer type. The pH of precipitation (pH*) corresponds to the value of the pH at which the absorbance suddenly increases to reach a value greater than 1.

In the present description, the term "test buffer solution Tp" is understood to mean an aqueous medium comprising 30 mg/g of bovine albumin fraction V (Aldrich), 0.01 M of phosphate buffer, 0.0027 M of potassium chloride, 0.137 M of sodium chloride (PBS from Aldrich) and 0.015 M of ammonium acetate (Aldrich).

In the present description, the term "Δn" is understood to mean the number of moles of sodium hydroxide necessary to bring 0.5 ml of the colloïdal solution comprising 1 mg of polymer PO from pHf to pH*, wherein said number is obtained by the conventional acid/base titration method TM:

A 2 mg/ml concentrated polyelectrolyte solution comprising 0.15 M of sodium chloride is brought to pH 4 by addition of acetic acid or 1M sodium hydroxide solution. This solution is subsequently titrated with a 0.05 M sodium hydroxide solution, and the change in pH is recorded as a function of the volume of sodium hydroxide added. The determination of Δn is performed by simply reading the volume of sodium hydroxide necessary to change the pH from pHf to pH*.

In the present description, the physiological pH is defined as being, for example, equal to 7.2±0.4.

In the present description, the term "polyelectrolyte" is understood to mean a polymer carrying groups capable of ionizing in water, thereby creating a charge on the polymer.

Q Test for Measuring the Retention Factor RQ:

A volume V of a preparation according to the invention, ready to be administrated, is added at 25° C. to 200 µl of a rat serum pool. After precipitation of the nanoparticles, the free protein concentration in the supernatant is measured by ELISA test.

By repeating the same test for increasing values of volume V, on can determine the V* value of the preparation volume for which the free-protein molar fraction in the supernatant is found to be greater than 10%.

The retention factor, RQ, is given by the ratio of the V* volume to 200 µl of rat serum.

For example, for V*=1 ml, RQ=5.

In order to evaluate the size of the particles of the colloïdal solution of polymer PO, it is preferable to use is the T' test. The result of the T' test is a mean hydrodynamic diameter.

T' Test for Measuring the Size of the Nanoparticles by Quasielastic Light Scattering:

The mean hydrodynamic diameter of particles of polymer according to the invention is measured according to the procedure Md defined below:

Polymer solutions are prepared at concentrations of 1 or 2 mg/ml in 0.15 M NaCl medium and are stirred for 24 h. These solutions are subsequently filtered through a 0.8-0.2 µm filter before analyzing them in dynamic light scattering using a device of Malvern Compact Goniometer System type operating with a vertically polarized He—Ne laser beam with a wavelength of 632.8 µm. The hydrodynamic diameter of the polymer nanoparticles is calculated from the autocorrelation function of the electric field by the method of cumulants, as described in the work "Surfactant Science Series", volume 22, Surfactant Solutions, edited by R. Zana, Chap. 3, M. Dekker, 1984.

In the present description, the term "nanoparticles" describes the particles which have a mean diameter of between 2 and 500 nm according to the T' test.

L Test for Measuring the Release of the Active Principle:

50 µl of formulation are injected into a cube with a side length of 1.5 cm, of polyurethane/polyether (PU-PE) foam bathed with a flow of 2.83 ml/h of an aqueous medium comprising 30 mg/g of bovine albumin fraction V (Aldrich), 0.01 M of phosphate buffer, 0.0027 M of potassium chloride, 0.137 M of sodium chloride (PBS from Aldrich) and 0.015 M of ammonium acetate (Aldrich). Samples are regularly withdrawn from the continuous phase, and the protein content of these samples is analyzed by ELISA.

It is then possible to plot the flow of protein by dividing the concentration measured by the flow rate imposed and the total weight of protein released by adding the values determined for each of the samples withdrawn.

Within the meaning of the invention, the term "protein" denotes a protein or a peptide, whether an oligopeptide or a polypeptide. This protein or this peptide may or may not be modified, for example, by grafting one or more polyoxyethylene groups.

Within the meaning of the invention, the expression "to carry" means that the group carried is pendant (or hanging), that is to say that said group is a side group with respect to the glutamic residues and is a substituent of the carbonyl functional group in the γ position of the glutamic residue which carries it.

Polyglutamates of the invention also carry cationic groups. These groups are grafted or linked to glutamic groups, preferably via an amide or ester bond.

Preferably, the polymer (PO) exhibits a structure $pGlu_{(x)}GH_{(y)}CG_{(z)}NG_{(1-x-y-z)}$ with a total degree of polymerization (DP) of between 50 and 300, preferably of between 100 and 250 and more preferably still of between 150 and 250.

According to an alternative form of the invention, the cationic groups (CG) can be selected from weak bases, the half-neutralization pH of which is less than 7.0.

Such cationic groups (CG) are obtained, for example, from histidine derivatives selected from the group consisting of histidine esters, preferably the methyl ester and the ethyl ester, histidinol, histamine, histidinamide, the N-monomethyl derivative of histidinamide and the N,N'-dimethyl derivative of histidinamide.

In this case, the values x, y and z can be such that x is between 0 and 45%, y is between 2 and 30%, z is between 40 and 98% and 1-x-y-z is between 0 and 50%.

It is also possible that the values x, y and z are such that x is between 0 and 45%, y is between 2 and 30%, z is between 40 and 60% and 1-x-y-z is between 0 and 58%.

It is also possible that the values x, y and z are such that x is between 0 and 45%, y is between 15 and 30%, z is between 40 and 60% and 1-x-y-z is between 0 and 45%.

If the polymer PO does not comprise neutral groups (NG), it is possible that the values x, y and z are such that x is between 0 and 45%, y is between 2 and 30% and z is between 40 and 98%.

According to another alternative form of the invention, the cationic groups (CG) can be selected from those which comprise at least one quaternary ammonium or at least one strong base, the half-neutralization pH of which is greater than 8.0.

Such cationic groups (CG) can be obtained from the following precursor compounds:
- a linear diamine comprising 2 to 6 carbons, preferably putrescine,
- agmatine,
- ethanolamine bonded via the oxygen,
- choline bonded via the oxygen,
- an ester or amide derivative of an amino acid, the side chain of which is positively charged at neutral pH, i.e. lysine, arginine or ornithine, bonded via the amine functional group in the α position.

In this case, the values x, y and z can be such that:
x is between 10 and 55%,
y is between 2 and 30%,
z is greater than or equal to 10% and is between (x−10) % and (x+15) %,
the number of neutral groups corresponding to the additional percentage in order to reach 100% and optionally being equal to 0.

It is also possible that the values x, y and z are such that:
x is between 20 and 55%,
y is between 2 and 7.5%,
z is greater than or equal to 20% and is between (x−10) % and (x+15) %,
the number of neutral groups corresponding to the additional percentage to reach 100% and optionally being able equal to 0.

It is also possible to choose the values x, y and z such that x is between 10 and 55%, y is between 2 and 30%, z is between 10 and 55%, and 1−x−y−z is between 0 and 60%.

It is also possible that the values x, y and z are such that x is between 10 and 20%, y is between 2 and 30%, z is between 10 and 30% and 1-x-y-z is between 20 and 78%.

It is also possible that the values x, y and z are such that x is between 10 and 20%, y is between 15 and 30%, z is between 10 and 30% and 1-x-y-z is between 20 and 65%.

If the polymer PO does not comprise neutral groups (NG), it is possible that the values x, y and z are such that x is between 10 and 55%, y is between 2 and 30% and z is between 40 and 60%.

Advantageously, the polyamino acids according to the invention are, e.g., α-L-glutamate or α-L-glutamic homopolymers.

The cationic groups which can be used to functionalize glutamate residues in the present invention are identical or different from one another and correspond to:

a histidine derivative selected from the group consisting of histidine esters, preferably the methyl ester and the ethyl ester, histidinol, histamine, histidinamide, the N-monomethyl derivative of histidinamide and the N,N'-dimethyl derivative of histidinamide or have:

the following general formula:

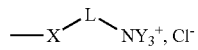

in which:

X=O or NH

Y=independently H or $CH_3$

L=a linear ($C_2$ to $C_6$) alkylene optionally substituted by a functional carboxyl group or a derivative thereof.

Thus, the cationic groups which can be used in the present invention can have one of the following formulae:

—NH—$(CH_2)_w$—$NH_3^+$, $Z^-$ in which w is between 2 and 6, and preferably w is 4,

—NH—$(CH_2)_4$—NH—C(=NH)—$NH_3^+$, $Z^-$,

—O—$(CH_2)_2$—$NH_3^+$, $Z^-$,

—O—$(CH_2)_2$—$N^+(CH_3)_3$, $Z^-$, an amino acid residue or an amino acid derivative of the formula:

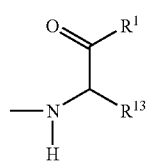

in which:

$R^1$ is an alkoxy, preferably —OMe or —OEt, or —$R^1$ is —$NH_2$, alkylamino, preferably —NH—$CH_3$ or —$N(CH_3)_2$;

$R^{13}$ is —$(CH_2)_4$—$NH_3^+$, $Z^-$, —$(CH_2)_3$—NH—C(=NH)—$NH_3^+$, $Z^-$, —$(CH_2)_3$—$NH_3^+$, $Z^-$;

in which $Z^-$ is a chloride, a sulfate, a phosphate or an acetate, preferably a chloride.

For example, the cationic groups can have the following formulae:

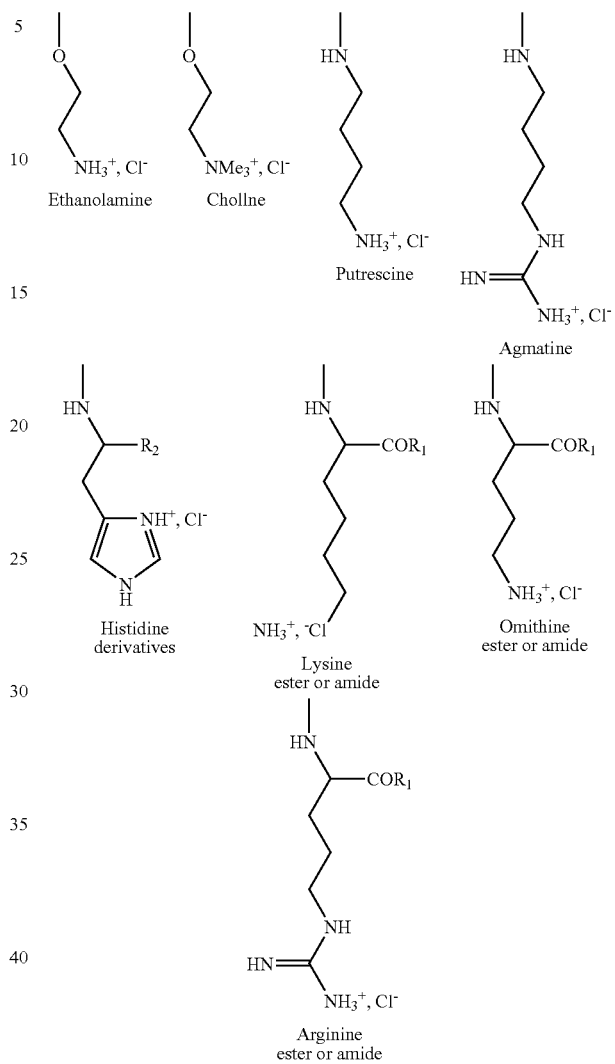

in which —$R_1$ is an alkoxy or alkylamino group, preferably —OMe, —OEt, —$NH_2$, —$NHCH_3$ or —$N(CH_3)_2$, and —$R_2$ is a hydrogen or —$CH_2OH$ or —C(=O)—$R^1$.

According to a preferred embodiment, an inventive polyamino acid comprises, on average, at least 3 hydrophobic groups (GH) per polymer chain.

Advantageously, at least one of the hydrophobic groups GH is included in a hydrophobic graft comprising at least one spacing joint (or residue) (spacer) which allows linkage of the hydrophobic group GH to a polyglutamate chain (for example, a polyglutamate backbone main chain). This joint can comprise, e.g., at least one direct covalent bond and/or at least one amide bond and/or at least one ester bond. For example, the joint can be of the type of those belonging to the group consisting of: "amino acid" residues other than the constituent monomeric residue of the polyglutamate, aminoalcohol derivatives, polyamine (for example diamine) derivatives, polyol (for example diol) derivatives and hydroxy acid derivatives.

The grafting of GHs to a polyglutamate chain can involve the use of GH precursors that can be linked to the polyglutamate chain.

The precursors of GHs are in practice, and without restriction, selected from the group consisting of alcohols and amines, which are easily functionalized one skilled in the art.

According to a preferred embodiment, a hydrophobic group GH of a hydrophobic graft comprises from 8 to 30 carbon atoms.

These hydrophobic groups GH are advantageously and carefully selected from the group consisting of:
- linear or branched $C_8$ to $C_{30}$ alkyls which can optionally comprise at least one unsaturation and/or at least one heteroatom,
- $C_8$ to $C_{30}$ alkylaryls or arylalkyls which can optionally comprise at least one unsaturation and/or at least one heteroatom, and
- $C_8$ to $C_{30}$ (poly)cyclic compounds which can optionally comprise at least one unsaturation and/or at least one heteroatom.

The joints which form, with the GHs, hydrophobic grafts can be di-, tri- or tetravalent joints (indeed even pentavalent and more). In cases of divalent joints, the hydrophobic graft comprises a single GH group, whereas a trivalent joint confers a bifid nature on the hydrophobic graft, that is to say that the graft exhibits two GH "arms". Examples of trivalent joints include "amino acid" residues, for example "glutamic acid", or polyol residues, for example glycerol. Thus, two advantageous but nonlimiting examples of hydrophobic grafts comprising bifid GHs are dialkylglycerols and dialkyl glutamates.

The hydrophobic groups GH can, for example, be derived from groups chosen from the group consisting of: octanol, dodecanol, tetradecanol, hexadecanol, octadecanol, oleyl alcohol, tocopherol and cholesterol.

As defined above, the neutral groups (NG) can be selected from the following group: a hydroxyethylamino-radical, a hydroxyalkyloxy-radical or a polyoxyalkylene.

According to another alternative form, the polyglutamates used in the present invention can also carry at least one graft of polyalkylene (preferably polyethylene) glycol type linked to a glutamate residue.

Preferably, the backbone of the polyglutamate according to the present invention comprises α-L-glutamate and/or α-L-glutamic acid residues.

More preferably still, the polyglutamates used in the present invention have the following formula (I):

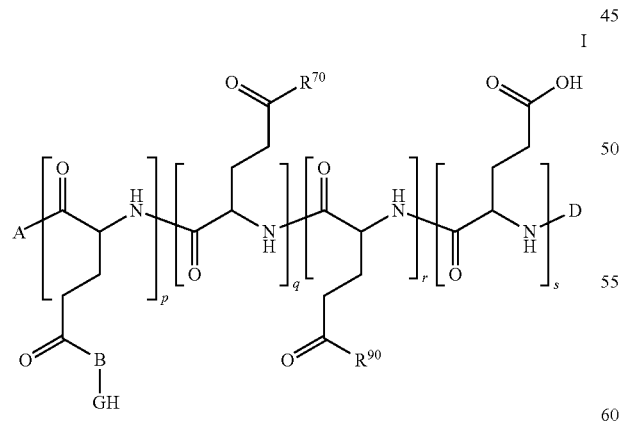

in which:
A independently is
   an NHR group in which R is H, a linear $C_2$ to $C_{10}$ or branched $C_3$ to $C_{10}$ alkyl or a benzyl,
   a terminal amino acid residue or a terminal amino acid derivative of formula:

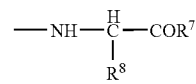

in which:
$R^7$ is OH, $OR^9$ or $NHR^{10}$,
and $R^8$, $R^9$ and $R^{10}$ independently are H, a linear $C_2$ to $C_{10}$ or branched $C_3$ to $C_{10}$ alkyl or a benzyl;
B is a direct bond or a divalent, trivalent or tetravalent bonding group preferably chosen from the following groups:
—O—, —NH—, —N($C_1$ to $C_5$ alkyl)-, an amino acid residue of amino acid (preferably of a natural amino acid), of diol, of triol, of diamine, of triamine, of aminoalcohol or of hydroxy acid comprising from 1 to 6 carbon atoms;
D is H, a linear $C_2$ to $C_{10}$ or branched $C_3$ to $C_{10}$ acyl group or a pyroglutamate;
the hydrophobic groups (GH) each are, independently of one another, a group chosen from:
   linear or branched $C_8$ to $C_{30}$ alkyls which can optionally comprise at least one unsaturation and/or at least one heteroatom (preferably O and/or N and/or S), or
   $C_8$ to $C_{30}$ alkylaryls or arylalkyls which can optionally comprise at least one unsaturation and/or at least one heteroatom (preferably O and/or N and/or S), or
   $C_8$ to $C_{30}$ (poly)cyclic compounds which can optionally comprise at least one unsaturation and/or at least one heteroatom (preferably O and/or N and/or S);
and preferably at least one of the hydrophobic groups (GH) is obtained, by grafting, from a precursor chosen from the group consisting of: octanol, dodecanol, tetradecanol, hexadecanol, octadecanol, oleyl alcohol, tocopherol and cholesterol, B representing a direct bond;
$R_{70}$ is a group selected from the following group:
—NH—$(CH_2)_n$—$NH_3^+$ in which w is between 2 to 6 and, preferably w is 4,
—NH—$(CH_2)_4$—NH—C(=NH)—$NH_3^+$,
—O—$(CH_2)_2$—$NH_3^+$,
—O—$(CH_2)_2$—$N+(CH_3)_3$,
a radical of the formula:

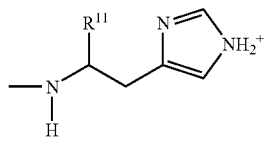

in which —$R^{11}$ represents —H, —$CO_2H$, an alkyl ester (preferably —COOMe and —COOEt), —C(=O)—$NH_2$, —C(=O)—NH—$CH_3$ or —C(=O)—$N(CH_3)_2$;
an amino acid residue or an amino acid derivative of the formula:

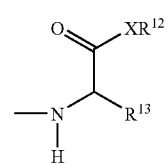

in which:

X is —O— or —NH—, $R^{12}$ is H, a linear $C_2$ to $C_{10}$ or branched $C_3$ to $C_{10}$ alkyl or a benzyl, —$R^{13}$ is —$(CH_2)_4$—$NH_3^+$, —$(CH_2)_3NH$—$C(=NH)$—$NH_3^+$, —$(CH_2)_3NH_3^+$; the counteranion of $R_{70}$ is an expedient group, in particular chosen from a chloride, a sulfate, a phosphate or an acetate, preferably a chloride;

$R_{90}$ is a hydroxyethylamino-, a hydroxyalkyloxy- or a polyoxyalkylene;

p, q, r and s are positive integers;

(p)/(p+q+r+s) is defined as the molar degree of grafting of the hydrophobic groups GH and varies from 2 to 30 molar %, provided that each copolymer chain has, on average, at least three hydrophobic grafts;

(q)/(p+q+r+s) is defined as the molar degree of grafting of the cationic groups and varies from 10 to 98 molar %;

(p+q+r+s) varies from 50 to 300, preferably between 100 and 250;

(r)/(p+q+r+s) varies from 0 to 78 molar %;

(s)/(p+q+r+s) varies from 0 to 55 molar %;

and encompass pharmaceutically acceptable salts thereof.

For further details on the preparation and synthesis of polyamino acids of formula (I) derived from histidine, see patent application FR 05 53302.

For further details on the preparation and synthesis of polyamino acids of formula (I) other than those derived from histidine, see French patent application FR 07 03185.

Preferably, the hydrophobic groups GH and the cationic groups are positioned randomly as pendant (or hanging) groups.

Generally, the general formula (I) described above should not be interpreted as representing solely block copolymers but also random copolymers or multiblock copolymers.

Preferably, the concentration of polymer (PO) in the formulation according to the invention can be between 4 and 50 mg/ml, in particular when the active principle (AP) is a therapeutic protein. Within this concentration range, the formulation can be easily injected by a needle with a small diameter, for example a needle of gauge 27 and even 29. Examples 2, 3 and 4 describe such formulations in detail.

Preferably, the concentration of polymer (PO) in a formulation according to the invention can be between 5 and 30 mg/ml and more preferably still between 5 and 15 mg/ml.

Advantageously, the ratio R of the concentration of active principle (AP) to the concentration of polymer (PO) can be between 0.0001 and 1.5. This ratio R can also be between 0.01 and 1.2.

According to an alternative form, the formulation according to the invention can comprise $Zn^{++}$ divalent cations in a proportion of between 0.05 and 2 molar equivalents with respect to the molar concentration of cationic groups (CG).

In particular, the formulation according to the invention can comprise added $Zn^{++}$ divalent cations in the proportion of between 0.25 and 0.75 molar equivalent with respect to the molar concentration of cationic groups (CG) and preferably equal to 0.5 eq., more particularly when the cationic groups (CG) are obtained from histidine derivatives chosen from the group consisting of histidine esters, preferably the methyl ester and the ethyl ester, histidinol, histamine, histidinamide, the N-monomethyl derivative of histidinamide and the N,N'-dimethyl derivative of histidinamide.

According to another alternative embodiment, a formulation according to the invention does not comprise added divalent cation.

The polymers used in the present invention have a molar mass which lies between 2 000 and 200 000 g/mol and preferably between 5 000 and 100 000 g/mol.

According to a particularly preferred embodiment of the invention, when the cationic groups (CG) are chosen from weak bases, the half-neutralization pH of which is less than 7.0, the polymers (PO) used in the invention exhibit a structure $pGlu_{(x)}GH_{(y)}CG_{(z)}NG_{(1-x-y-z)}$ such that x is between 0 and 20%, y is between 2 and 30%, z is between 60 and 95% and 1-x-y-z is between 0 and 15%.

It is also possible that the values x, y and z are such that x is between 0 and 20%, y is between 2 and 10%, z is between 75 and 95% and 1-x-y-z is between 0 and 15%.

It is also possible that the values x, y and z are such that x is between 0 and 20%, y is between 15 and 25%, z is between 60 and 80% and 1-x-y-z is between 0 and 15%.

If the polymer PO does not comprise neutral groups (NG), it is possible that the values x, y and z are such that x is between 0 and 20%, y is between 2 and 30% and z is between 60 and 95%.

According to another preferred embodiment of the invention, when the cationic groups (CG) are chosen from groups comprising quaternary ammoniums or at least one strong base, the half-neutralization pH of which is greater than 8.0, the values x, y and z can be such that x is between 15 and 50%, y is between 2 and 30%, z is between 10 and 50% and 1-x-y-z is between 10 and 55%.

It is also possible that the values x, y and z are such that x is between 15 and 30%, y is between 2 and 30%, z is between 15 and 25% and 1-x-y-z is between 40 and 55%.

It is also possible that the values x, y and z are such that x is between 25 and 50%, y is between 2 and 30%, z is between 25 and 50% and 1-x-y-z is between 10 and 30%.

If the polymer PO does not comprise neutral groups (NG), it is possible that the values x, y and z are such that x is between 10 and 55%, y is between 2 and 30% and z is between 40 and 60%.

Due to an excess of cationic charge, the polymer PO used in the invention is cationic and soluble at the pHf value of the formulation. This charge is partially or completely neutralized at neutral pH, so that the polymer precipitates. Without being restricted by theory, it may be supposed that this phenomenon of precipitation induced by an increase in the pH results from the decrease in the overall charge to the polymers between the formulation pH and the physiological pH and from the presence of hydrophobic side groups.

It should be understood that the residual carboxyl functional groups of the modified polyglutamate are either neutral (COOH form) or ionized (COO⁻ anion), depending on the pH and the composition. So, both terms i) glutamate residue or residue of glutamic acid or ii) polyglutamic acid or polyglutamate can be used interchangeably.

Similarly, the amino groups will mainly be ionized at any pH below their pKa and the quaternary ammoniums will be ionized at any pH.

In aqueous solution, the countercation can be a metal cation, such as sodium, calcium or magnesium, or an organic cation, such as triethanolamine, tris(hydroxymethyl)-aminomethane or a polyamine, such as polyethyleneimine. If it is divalent, the countercation can salify two closed monovalent anionic groups.

The counteranion of the cationic groups is preferably chosen from the group consisting of a chloride, a sulfate, a phosphate or an acetate.

If it is divalent, the counteranion can salify two closed monovalent cationic groups.

In the present description, the term "pharmaceutically acceptable salts" of a polymer according to the invention is understood to encompass all the polymers with counterions associated with ionized functions of the polymer.

The polyamino acids suitable for use in the present invention are obtained, for example, by methods known to a person skilled in the art. First of all, it should be remembered that the most widely used technique for obtaining polyamino acid of a type is based on the polymerization of N-carboxyamino acids anhydrides (NCA), described, for example, in the paper "*Biopolymers*, 1976, 15, 1869" and in the work by H. R. Kricheldorf "*alpha-Amino acid N-carboxy Anhydride and related Heterocycles*", Springer Verlag (1987). The NCA derivative is preferably NCA-Glu-O—$R_3$ ($R_3$=methyl, ethyl or benzyl). The polymers are subsequently hydrolyzed under appropriate conditions for obtaining the polymer in its acid form. These methods are inspired by the description given in patent FR-A-2 801 226 of the Applicant.

A certain number of polymers which can be used according to the invention, for example of poly($\alpha$-L-glutamic), poly($\alpha$-D-glutamic), poly($\alpha$-D,L-glutamate) and poly($\gamma$-L-glutamic) type with variable weights, are available commercially.

The coupling of the GH graft with an acid group of the polymer is easily carried out by reaction of the polyamino acid in the presence of a carbodiimide as coupling agent and optionally a catalyst, such as 4-dimethylaminopyridine, and in an appropriate solvent, such as dimethylformamide (DMF), N-methylpyrrolidone (NMP) or dimethyl sulfoxide (DMSO). The carbodiimide is, for example, dicyclohexylcarbodiimide or diisopropylcarbodiimide. The degree of grafting is chemically controlled by the stoichiometry of the constituents and reactants or the reaction time. The hydrophobic grafts functionalized by a "spacer" are obtained by conventional peptide coupling or by direct condensation by acid catalysis.

The coupling of the cationic and optionally neutral groups with an acid functional group of the polymer is carried out simultaneously in a second stage in the presence of a chloroformate as coupling agent and in an appropriate solvent, such as dimethylformamide, N-methylpyrrolidone (NMP) or dimethyl sulfoxide (DMSO).

In cases where the cationic group comprises two amino groups which are not chemically differentiated (e.g., linear diamine), it can be introduced in a form in which one of the two functional groups is protected. A final stage of cleavage of the protective group is then added.

The polymerization chemistry and reactions for coupling the groups are conventional and well known to a person skilled in the art (see, for example, the patents or patent applications of the Applicant mentioned above).

Examples of the preparation of formulations according to the invention are described in detail in the examples, to which reference will be made.

The characteristics of the formulation according to the invention stated above make it possible for a person skilled in the art to select, from all the formulations based on polymer PO, those which simultaneously satisfy the conditions (a), (b), (c) and (d) and which, for this reason, correspond best to the requirements defined in the preamble.

Conditions (c) and (d) are particularly selective. If the formulation does not form a colloïdal solution at pHf, a person skilled in the art will select a polymer exhibiting, at this pH value, a greater number of nonionized monomers. If, on the other hand, the polymer precipitates, it would be advisable to increase the number of ionized monomers at this pH.

It is important to point out that, counterintuitively, some formulations which result in colloïdal solutions at pHf and which precipitate at physiological pH should, however, be excluded as not satisfying condition (d). Thus, condition (d) is a convenient means for a person skilled in the art to select formulations according to the invention.

It is important to point out that condition (d) implies that the formulation according to the invention precipitates for a pH value less than or equal to the physiological pH. This is because, after mixing 1 ml of the acid formulation according to the invention and 1 ml of the buffer solution Tp, precipitation should be observed at a pH value less than or equal to the pH of the buffer solution, that is to say <7.2.

A second method of selecting formulations according to the invention is to estimate its precipitation factor PF. This factor is evaluated in the following way:

a) Measurement of the Precipitation pH, Recorded as pH*

At acidic pHf between 3 and 6.5, the colloïdal solution loaded with AP exists as a clear liquid comprising nanoparticles, the mean hydrodynamic diameter of which, measured by dynamic light scattering according to the T' test, is less than or equal to 0.5 µm, preferably between 5 and 500 nm, more preferably between 10 and 80 nm. When the pH is increased, the solution according to the invention must precipitate for a pH value less than or equal to the physiological pH. The value pH* for which the solution precipitates is measured according to the P test.

b) Determination of PF

Measurement of the number of moles of sodium hydroxide, $\Delta n$, necessary to bring 0.5 ml of the colloïdal solution comprising 1 mg of polymer PO from pHf to pH* according to the TM method.

By denoting C as the concentration of polymer PO in the formulation (expressed in mg/g) and y the molar fraction of monomer of the polymer PO carrying the hydrophobic side graft, the precipitation factor PF of the formulation is calculated by the formula:

$$PF = \frac{y}{\Delta n \cdot C}$$

Examples of the calculation of the precipitation factor PF are given in the examples.

In a specific implementation of the invention, the formulations according to the invention are characterized by a precipitation factor PF of greater than 200, preferably of greater than 400, more preferably of greater than 800 and more preferably still of greater than 1500.

A surprising aspect of the formulations according to the invention is that the network of chains of polymers which is formed during the precipitation at physiological pH makes it possible to slow down the release of the active principle (AP) without, however, trapping this same active principle (AP) at the core of the particles. Thus, the formulations according to the invention make it possible to obtain both sustained release of the active principle (AP) and good bioavailability.

The active principle (AP) is preferably chosen from the group consisting of: proteins, glycoproteins, proteins bonded to one or more polyalkylene glycol chains [preferably polyethylene glycol (PEG): "PEGylated proteins"], peptides, polysaccharides, liposaccharides, oligonucleotides, polynucleotides and mixtures thereof, and, more preferably still, from the subgroup of erythropoietins, such as epoetin alfa, epoetin beta, darbepoetin, hemoglobin raffimer, their analogs or their derivatives; oxytocin, vasopressin, adrenocorticotropic hormone, epidermal growth factor, platelet-derived growth factor (PDGF), factors which stimulate hematopoiesis and mixtures thereof, blood factors, such as alteplase, tenecteplase, factor VII(a) or factor VII; hemoglobin, cytochromes, albumins, prolactin, luliberin, luteinizing hormone-releasing hormone (LHRH) and analogs, such as leuprolide, goserelin, triptorelin, buserelin or nafarelin; LHRH antagonists, LHRH competitors, human, porcine or bovine growth hormones (GHs), growth hormone-releasing factor, insulin, somatostatin, glucagon, interleukins or their mixtures (IL-2, IL-11, IL-12), interferons, such as interferon alfa, alfa-2b, beta, beta-1a or gamma; gastrin, tetragastrin, pentagastrin, urogastrone, secretin, calcitonin, enkephalin, endomorphins, angiotensins, thyrotropin-releasing hormone (TRH), tumor necrosis factor (TNF), nerve growth factor (NGF), growth factors, such as beclapermin, trafermin, ancestim or keratinocyte growth factor, granulocyte-colony stimulating factor (G-CSF), granulocyte-macrophage-colony stimulating factor (GM-CSF), macrophage-colony stimulating factor (M-CSF), heparinase, bone morphogenetic protein (BMP), hANP, glucagon-like peptide (GLP-1), VEG-F, recombinant hepatitis B surface antigen (rHBsAg), renin, cytokines, bradykinin, bacitracins, polymyxins, colistins, tyrocidine, gramicidins, etanercept, imiglucerase, drotrecogin alfa, cyclosporins and synthetic analogs, pharmaceutically active modifications and fragments of enzymes, of cytokines, of antibodies, of antigens and of vaccines, and antibodies, such as rituximab, infliximab, trastuzumab, adalimumab, omalizumab, tositumomab, efalizumab and cetuximab.

Other suitable active principles are polysaccharides (for example heparin) and oligo- or polynucleotides, DNA, RNA, iRNA, antibiotics and living cells. Another category of active principles comprises pharmaceutical substances which act on the central nervous system, for example risperidone, zuclopenthixol, fluphenazine, perphenazine, flupentixol, haloperidol, fluspirilene, quetiapine, clozapine, amisulpride, sulpiride, ziprasidone, and the like.

According to an alternative embodiment, the active principle is a hydrophobic, hydrophilic or amphiphilic small organic molecule belonging to the family of anthracyclines, taxoids or camptothecins or belonging to the family of peptides, such as leuprolide or cyclosporin, and mixtures thereof.

According to another alternative embodiment, the active principle is advantageously chosen from at least one of the following families of active substances: agents for the treatment of alcohol abuse, agents for the treatment of Alzheimer's disease, anesthetics, agents for the treatment of acromegaly, analgesics, antiasthmatics, agents for the treatment of allergies, anticancer agents, antiinflammatories, anticoagulants and antithrombotics, anticonvulsants, antiepileptics, antidiabetics, antiemetics, antiglaucomas, antihistaminics, antiinfectives, antibiotics, antifungals, antivirals, antiparkinsonians, anticholinergics, antitussives, carbonic anhydrase inhibitors, cardiovascular agents, hypolipidemics, antiarrythmics, vasodilators, antianginals, antihypertensives, vasoprotectants, cholinesterase inhibitors, agents for the treatment of disorders of the central nervous system, stimulants of the central nervous system, contraceptives, fertility promoters, inducers and inhibitors of uterine labor, agents for the treatment of mucoviscidosis, dopamine receptor agonists, agents for the treatment of endometriosis, agents for the treatment of erectile dysfunctions, agents for the treatment of fertility, agents for the treatment of gastrointestinal disorders, immunomodulators and immunosuppressants, agents for the treatment of memory disorders, antimigraines, muscle relaxants, nucleoside analogs, agents for the treatment of osteoporosis, parasympathomimetics, prostaglandins, psychotherapeutic agents, sedatives, hypnotics and tranquilizers, neuroleptics, anxiolytics, psychostimulants, antidepressants, agents for dermatological treatments, steroids and hormones, amphetamines, anorectics, nonanalgesic painkillers, barbiturates, benzodiazepines, laxatives, psychotropics and any combination of these products.

The formulation according to the invention can be administered orally, parenterally, nasally, vaginally, ocularly, subcutaneously, intraveneously, intramuscularly, interaderally, transdermally, intraperitoneally, intracerebrally or buccally.

According to another aspect, the present invention provides a process for the preparation of formulations based on polymer PO for the sustained release of at least one active principle, these formulations being in particular those described above, said process comprising the following steps:

1) preparing, at a pH value of between 3 and 6.5, an aqueous colloïdal solution of a polyamino acid polymer (PO) as defined above, the respective molar fractions of cationic group (CG), hydrophobic group (GH), optionally neutral groups (NG) and optionally glutamate being such that 1 ml of said formulation precipitates during mixing with a volume of 1 ml of a test buffer solution Tp; and 2) adding at least one active principle (AP) to the polymer (PO) obtained in step 1, said active principle associating noncovalently with particles of the colloïdal solution of said polymer (PO).

An essential characteristic of the process according to the invention is that of spontaneously formation of particles loaded with active principle at a pHf of between 3 and 6.5 by simple mixing of a colloïdal solution of particles of the polyelectrolyte polymer (PO) and of the active principle (AP).

The active principles, such as proteins, peptides or small molecules, can associate spontaneously with the polymer (PO) of polyamino acid type.

In a specific implementation of the invention, the loading of nanoparticles of the polyelectrolyte polymer (PO) by an active principle (AP) is carried out by simple mixing of a solution of active principle (AP) with a colloïdal solution of the polyelectrolyte polymer (PO). This association is purely physical and does not involve the creation of a covalent bond between the active principle (AP) and the polymer (PO). Without being restricted by theory, it may be supposed that this nonspecific association takes place by hydrophobic and/or electrostatic interactions between the polymer (PO) and the active principle (AP). It should be noted that it is unnecessary, and often even undesirable, to bind the AP to the PO nanoparticles via specific receptors of peptide nature or of antigene/antibody or also enzyme/substrate type.

In a preferred embodiment of the process according to the invention, the process does not comprise a step of chemical crosslinking of the particles obtained. Thus, the particles obtained are not chemically crosslinked and nevertheless release the active principle (AP) over a sustained period of time. This absence of chemical crosslinking is a decisive advantage. This is because the absence of chemical crosslinking makes it possible to avoid chemical decomposition of the active principle (AP) that could happen during a step of crosslinking of the particles comprising the active principle (AP). This is because such a chemical crosslinking is generally carried out by activation of polymerizable entities and involves potentially denaturing agents, such as UV radiation or glutaraldehyde.

Advantageously, the process according to the invention comprises a step of dehydration, for example by lyophilization, of the liquid formulation in order to obtain a formulation in the form of a dry powder.

The present invention also relates to a solid pharmaceutical formulation for the sustained release of at least one active principle (AP) comprising a dry powder form obtained from the liquid formulation comprising an aqueous suspension mentioned above.

A dry powder can be obtained by bringing the liquid formulation according to the invention to a pH equal to 7, in order to precipitate it in vitro, and by then dehydrating it, for example by lyophilization.

Advantageously, such a solid pharmaceutical formulation is used for inhalation and pulmonary administration.

According to another aspect, a subject matter of the invention is a process for the preparation of medicaments, in particular for parenteral, mucosal, subcutaneous, intramuscular, intradermal, transdermal, intraperitoneal or intracerebral administration or administration into a tumor, by the oral, nasal, pulmonary, vaginal or ocular route, said process consisting essentially in employing at least one of the formulations described above.

BRIEF DESCRIPTION OF THE FIGURES

FIG. 1: in vitro release of IFN-α from the formulations described in example 2.1 (black triangles), example 2.3 (black diamonds), example 3 (black squares) and example 5 (solid line).

EXAMPLES

1) Syntheses a) Comparison: Synthesis of an Anionic Polyelectrolyte Polymer PO Carrying Hydrophobic Groups (Polyglutamate Grafted with α-tocopherol of Synthetic Origin)

15 g of an α-L-polyglutamic acid with a weight equivalent to approximately 16 900 Da with respect to a polyoxyethylene standard are dissolved in 288 ml of dimethylformamide (DMF) while heating at 80° C. until the polymer has dissolved. The solution is cooled to 15° C. and 2.5 g of D,L-α-tocopherol (>98%, obtained from Fluka®), dissolved beforehand in 8 ml of DMF, 280 mg of 4-dimethylaminopyridine, dissolved beforehand in 1 ml of DMF, and 1.6 g of diisopropylcarbodiimide, dissolved beforehand in 6 ml of DMF, are successively added. After stirring for 3 hours, the reaction medium is poured into 1200 ml of water comprising 15% of sodium chloride and hydrochloric acid (pH 2). The precipitated polymer is subsequently recovered by filtration and washed with 0.1N hydrochloric acid, with water and with diisopropyl ether. The polymer is subsequently dried in an oven under vacuum at 40° C. A yield of the order of 90% is obtained. The molar mass, measured by steric exclusion chromatography, is 15 500, with respect to a polyoxyethylene standard. The level of grafted tocopherol, estimated by proton NMR spectroscopy, is 5.1 molar %.

b) Synthesis of a Cationic Polyelectrolyte Polymer PO-A1 (Polyglutamate Grafted with α-tocopherol of Synthetic Origin and with Histidinamide)

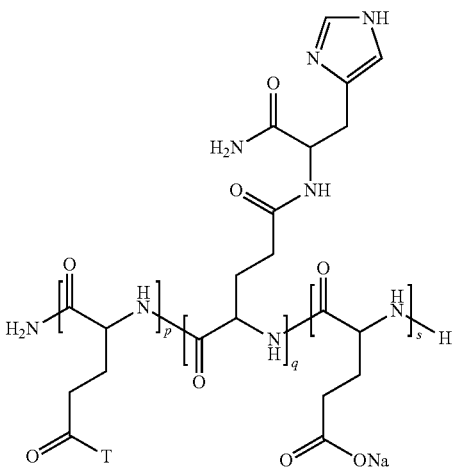

Indices and groups: p=11, q=209, s=0, T=D,L-α-tocopherol (T)

3 g of a poly(glutamic acid) with a DP of 220 randomly grafted with 5% of racemic α-tocopherol are dissolved by heating at 80° C. in 38 ml of NMP. This solution is cooled to 0° C. and 2.74 g of isobutyl chloroformate and then 2.2 ml of N-methylmorpholine are added. The reaction medium is stirred for 10 minutes while maintaining the temperature at 0° C. At the same time, 8.65 g of histidinamide dihydrochloride are suspended in 108 ml of NMP. 10.6 ml of triethylamine are subsequently added and the suspension obtained is stirred at 20° C. for a few minutes and then cooled to 0° C. The solution of activated polymer is subsequently added to the histidinamide suspension. The reaction medium is stirred at 0° C. for 2 hours and then at 20° C. overnight. 0.62 ml of 35% HCl and then 83 ml of water are subsequently added. The solution obtained is subsequently poured into 500 ml of water at pH 3-4. The solution is subsequently diafiltered against 8 volumes of aqueous saline solution (0.9% NaCl) and 4 volumes of water. The polymer solution is subsequently concentrated to a volume of 300 ml (the polymer concentration is 18 mg/g). The percentage of grafted histidinamide, determined by $^1$H NMR in $D_2O$, is 95%.

c) Synthesis of a Cationic Polyelectrolyte Polymer PO-A2 (Polyglutamate Grafted with α-tocopherol of Synthetic igin and with Histidinamide)

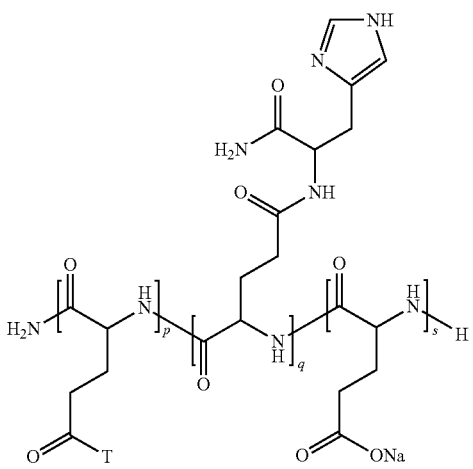

Indices and groups: p=44, q=154, s=22, T=D,L-α-tocopherol (T)

10 g of a poly(glutamic acid) with a DP of 220 randomly grafted with 20% of racemic α-tocopherol are dissolved by heating at 80° C. in 125 ml of NMP. This solution is cooled to 0° C. and 5.5 g of isobutyl chloroformate and then 4.4 ml of N-methylmorpholine are added. The reaction medium is stirred for 10 minutes while maintaining the temperature at 0° C. At the same time, 12.9 g of histidinamide dihydrochloride are suspended in 161 ml of NMP. 15.8 ml of triethylamine are subsequently added and the suspension obtained is stirred at 20° C. for a few minutes and then cooled to 0° C. The solution of activated polymer is subsequently added to the histidinamide suspension. The reaction medium is stirred at 0° C. for 2 hours and then at 20° C. overnight. 1.46 ml of 35% HCl and then 200 ml of water are subsequently added. A further 200 ml of water are added, followed by 650 ml of ethanol, and pouting is subsequently carried out into 650 ml of water at pH 3-4. The solution is subsequently diafiltered against 8 volumes of aqueous saline solution (0.9% NaCl) and 4 volumes of water. The polymer solution is finally concentrated to a volume of 250 ml (the polymer concentration is 50 mg/g). The percentage of grafted histidinamide, determined by $^1$H NMR in $D_2O$, is 70%.

d) Synthesis of a Cationic Polyelectrolyte Polymer PO-B (Polyglutamate Grafted with α-tocopherol of Synthetic Origin, with Ethanolamine and with Argininamide)

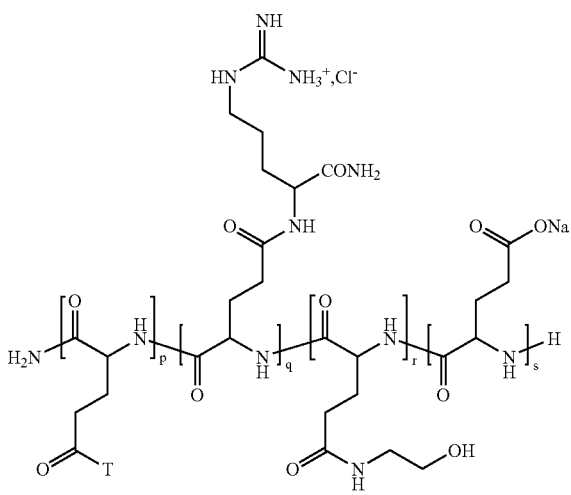

Indices and groups: T=D,L-α-tocopherol, p=11, q=88, r=48, s=73

Ten grams of a poly(glutamic acid) with a DP of 220 randomly grafted with 5% of racemic α-tocopherol are dissolved in 125 ml of NMP at 80° C. This solution is cooled to 0° C. and 5.6 ml of isobutyl chloroformate and then 4.8 ml of N-methylmorpholine are added. This reaction mixture is stirred at 0° C. for 15 minutes. At the same time, 7.4 g of argininamide dihydrochloride are suspended in 93 ml of NMP and then 4.7 ml of triethylamine and 1.2 ml of ethanolamine are added. The suspension obtained is stirred at 20° C. for a few minutes and then cooled to 0° C. The milky suspension of activated polymer is then added to this suspension and the reaction mixture is stirred at 0° C. for 2 h and then at 20° C. overnight. After addition of 2.07 ml of a 35% HCl solution and then 200 ml of water, the reaction mixture is run dropwise into 670 ml of water acidified to pH=3 with HCl, the pH being maintained at approximately 3 with a 1N HCl solution. The solution obtained is diafiltered against 8 volumes of aqueous saline solution (0.9%) and then 4 volumes of water, and concentrated to a volume of approximately 250 ml. The percentages of grafted argininamide and of grafted ethanolamine, determined by proton NMR in $D_2O$, are respectively 40 and 22%.

2) Example 1 (Comparative)

Formulation Based on Polymer PO not Carrying Cationic Derivative (Synthesis a)

The polymer PO obtained according to synthesis a) above is used.

A 24 mg/g colloïdal solution of polymer PO is obtained by diluting 12.64 g of PO solution with 2.19 g of water. The osmolarity of the colloïdal PO solution and its pH are subsequently adjusted to 290 mOsm and pH 6.95 by respectively introducing the necessary amounts of an aqueous NaCl solution and of a NaOH solution.

The characteristics of the formulation obtained are combined in the table below:

The size of the particles is measured according to the T' test.

| [PO] (mg/g) | pH | Osmolarity (mOsm) | Size (nm) |
|---|---|---|---|
| 23.14 | 6.95 | 290 | 40 |

The formulation based on polymer PO described above does not precipitate during the addition of 1 ml of the latter to 1 ml of buffer solution Tp.

3) Example 2

Formulation Based on Polymer PO-A1

3.1) Example 2.1

Concentration of PO-A1 Equal to 10 mg/g, Comprising IFN-α a) Preparation of a Colloïdal Solution of PO-A1
The polymer PO-A1 obtained according to synthesis b) above is used.
The PO-A1 is diluted in water and the pH is adjusted (appropriate NaOH solution) and the osmolarity is adjusted (appropriate NaCl solution).

| [PO-A1] (mg/g) | pH | Osmo (mOsm) |
|---|---|---|
| 12.93 | 5.98 | 231 |

The colloïdal solution based on polymer PO-A1 obtained precipitates during the addition of 1 ml of the latter to 1 ml of buffer solution Tp and it is characterized by a precipitation factor PF=860. The polymer PO-A1 is characterized by a pH* equal to 6.5.

b) Association of the Protein with the Polymer PO-A1
2.18 g of the 2.4 mg/g protein IFN-α are added to 8 g of colloïdal solution of PO-A1 and the final concentration is adjusted by diluting with an appropriate NaCl solution (0.18 g).

c) Association Overnight at 25° C.

The characteristics of the final formulation are combined in the table below:
The size of the particles is measured according to the T' test.

| [polymer] (mg/g) | [IFN-α] (mg/g) | pH | Osmo (mOsm) | Size (nm) |
|---|---|---|---|---|
| 10 | 0.5 | 5.9 | 313 | 34 |

3.2) Example 2.2

Concentration of PO-A1 Equal to 45 mg/g

The polymer PO-A1 obtained according to synthesis b) above is used.
The PO-A1 is diluted in water and the pH is adjusted (appropriate NaOH solution) and the osmolarity is adjusted (appropriate NaCl solution).

| [PO-A1] (mg/g) | pH | Osmo (mOsm) | Size (nm) |
|---|---|---|---|
| 45.3 | 5.5 | 299 | 37 |

The colloïdal solution based on polymer PO-A1 obtained does not precipitate during the addition of 1 ml of the latter to 1 ml of buffer solution Tp and is characterized by a precipitating factor PF equal to 166.

3.3) Example 2.3

Concentration of PO-A1 Equal to 10 mg/g, Comprising IFN-α and $Zn^{++}$ Cations a) Preparation of a Colloïdal Solution of PO-A1 Comprising 0.5 eq. $Zn^{++}$
The polymer PO-A1 obtained according to synthesis b) above is used.
The PO-A1 is diluted in water and the pH is adjusted (appropriate NaOH solution) and the osmolarity is adjusted (appropriate NaCl solution).

| [PO-A1] (mg/g) | pH | Osmo (mOsm) |
|---|---|---|
| 13.11 | 4.63 | 210 | b) Association of the Protein with the Polymer PO-A1
2.17 g of the 2.4 mg/g protein IFN-α are added to 7.96 g of colloïdal solution of PO-A1 prepared in stage a) and the final concentration is adjusted by diluting with an appropriate NaCl solution (0.18 g).
c) Association Overnight at 25° C.
d) Addition of the $Zn^{++}$ Cations
The necessary amount of 204 mg/g concentrated $ZnCl_2$ solution is added to the preceding formulation in order to achieve 0.5 molar equivalent of $Zn^{++}$ cations per cationic derivative present in solution.
The characteristics of the final formulation are combined in the table below:
The size of the particles is measured according to the T' test.

| [polymer] (mg/g) | [IFN-α] (mg/g) | [$Zn^{++}$] (eq.) | pH | Osmo (mOsm) | Size (nm) |
|---|---|---|---|---|---|
| 10.02 | 0.5 | 0.51 | 4.05 | 337 | 36 |

The colloïdal solution based on polymer PO-A1 obtained precipitates during the addition of 1 ml of the latter to 1 ml of buffer solution Tp and is characterized by a precipitating factor PF equal to 860. The polymer PO-A1 comprising 0.5 molar equivalent of $Zn^{++}$ cations per cation derivative is characterized by a pH* equal to 4.8.

4) Example 3

Formulation Based on 30 mg/g of Polymer PO-A2 Comprising IFN-α a) Preparation of a Colloïdal Solution of PO-A2
The polymer PO-A2 obtained according to synthesis c) above is used.
The PO-A2 is diluted in water and the pH is adjusted (appropriate NaOH solution) and the osmolarity is adjusted (appropriate NaCl solution).

| [PO-A2] (mg/g) | pH | Osmo (mOsm) |
|---|---|---|
| 38.52 | 6.04 | 237 |

The colloïdal solution based on polymer PO-A2 obtained precipitates during the addition of 1 ml of the latter to 1 ml of buffer solution Tp and is characterized by a precipitation factor PF equal to 840. The polymer PO-A2 is characterized by a pH* equal to 6.5.
b) Association of the Protein with the Polymer PO-A2
2.18 g of the 2.4 mg/g protein IFN-α are added to 8 g of colloïdal solution of PO-A2 and the final concentration is adjusted by diluting with an appropriate NaCl solution (0.18 g).
c) Association Overnight at 25° C.
The characteristics of the final formulation are combined in the table below:
The size of the particles is measured according to the T' test.

| [polymer] (mg/g) | [IFN-α] (mg/g) | pH | Osmo (mOsm) | Size (nm) |
|---|---|---|---|---|
| 29.8 | 0.5 | 5.8 | 320 | 35 |

5) Example 4

Formulation Based on Polymer PO-B Comprising or not IFN-α

5.1) Example 4.1

Concentration of PO-B Equal to 10 mg/g Comprising IFN-α a) Preparation of a Colloïdal Solution of PO-B
The polymer PO-B obtained according to synthesis d) above is used.
The PO-B is diluted in water and the pH is adjusted (appropriate NaOH solution) and the osmolarity is adjusted (appropriate NaCl solution).

| [PO-B] (mg/g) | pH | Osmo (mOsm) |
|---|---|---|
| 11.2 | 4.17 | 275 |

The colloïdal solution based on polymer PO-B obtained precipitates during the addition of 1 ml of the latter to 1 ml of buffer solution Tp and is characterized by a precipitation factor PF equal to 1150. The polymer PO-B is characterized by a pH* equal to 5.

b) Association of the Protein with the Polymer PO-B 1.8 g of the 2.7 mg/g protein IFN-α are added to 8 g of colloïdal solution of PO-B, and the final concentration is adjusted by diluting with an appropriate NaCl solution.

c) Association Overnight at 25° C.

The size of the particles is measured according to the T' test.

The characteristics of the final formulation are combined in the table below:

| [polymer] (mg/g) | [IFN-α] (mg/g) | pH | Osmolarity (mOsm) |
|---|---|---|---|
| 9.3 | 0.5 | 4.2 | 293 |

The formulation as made above is characterized in the Q test by a retention factor RQ greater than 5 (ELISA test of the percentage of free —IFN-α for RQ=5:8%.

5.2) Example 4.2

Concentration of PO-B Equal to 45 mg/g

The polymer PO-B obtained according to synthesis d) above is used.

The PO-B is diluted in water and the pH is adjusted (appropriate NaOH solution) and the osmolarity is adjusted (appropriate NaCl solution).

| [PO-B] (mg/g) | pH | Osmo (mOsm) | Size (nm) |
|---|---|---|---|
| 45 | 4 | 294 | 35 |

The colloïdal solution based on polymer PO-B obtained precipitates during the addition of 1 ml of the latter to 1 ml of buffer solution Tp and is characterized by a precipitation factor PF equal to 256. The polymer PO-B is characterized by a pH* equal to 5.

6) Example 5 (Comparative)

Preparation of Particles Based on PO, Comprising IFN-α

The polymer PO obtained according to synthesis a) above is used.

A colloïdal solution of polymer PO is obtained by dissolving it in water, the pH being adjusted to 7.52 by addition of a NaOH solution. The osmolarity of the solution is adjusted to 108 mOsm by introducing the necessary amount of an aqueous NaCl solution. The concentration of polymer PO is adjusted to 29.05 mg/g.

Concentrated 2.4 mg/g protein IFN-α is added to the preceding colloïdal solution of polymer PO. The association is produced at 25° C. overnight.

The characteristics of the particles obtained are combined in the table below:

The size of the particles is measured according to the T' test.

| [PO] (mg/g) | [IFN-α] (mg/g) | pH | Osmolarity (mOsm) | Size (nm) |
|---|---|---|---|---|
| 23 | 0.5 | 7.20 | 300 | 40 |

7) In Vitro Results for Examples 2, 3 and 5

For this, the release of the active principle from the formulations according to the invention is measured using the L test.

The release in the L test is shown in FIG. 1 in the form of the percentage of protein released over time.

The formulation of comparative example 5, comprising 23 mg/g of PO particles, exhibits a release profile characterized by 93% of protein released in 10 hours.

The formulations of examples 2.1 and 3 exhibit delayed-release profiles with releases respectively of 67% and 65% of the injected protein in 48 hours.

In the case of the particles of example 2.3, the creation of a release flow is observed which is not zero at the end of the experiment, with a release of 59% of the injected protein in 48 hours.

8) In Vivo Results for Examples 2, 3 and 5

44 rats were separated into 5 groups of 8 or 12 animals and received, in parallel, an immediate release IR formulation or a sustained release formulation corresponding to comparative example 5 or one of the formulations of examples 2 and 3 of the invention, at the dose of 300 µg/kg.

The pharmacokinetic results are combined in the table below:

| Example | N | $C_{max}$ (ng/ml) | $T_{max}$ median (interval) (hour) | AUC (ng × h/ml) | $T50\%_{AUC}$ (h) | RBA (%) |
|---|---|---|---|---|---|---|
| IFN IR (0.5) | 12 | 100.6 | 05 (0.25-1) | 255.9 | 1.5 | 100 |
| Ex 2.1 | 8 | 3.6 | 3 (3-24) | 135.4 | 24.7 | 57 |
| Ex 2.3 | 8 | 1.1 | 3 (3-24) | 28.3 | 19.4 | 12 |
| Ex 3 | 8 | 26.2 | 3 (3-6) | 264.8 | 7.1 | 111 |
| Ex 5 | 8 | 3.5 | 12 (6-24) | 95.7 | 18.4 | 62 |

$C_{max}$ represents the mean maximum plasma concentration of protein for all the animals.
$T_{max}$ median represents the median of the time for which the plasma concentration passes through its maximum.
AUC represents the mean area under the curve of the plasma concentration as a function of time.
$T50\%_{AUC}$ represents the mean time at the end of which the area under the curve reaches 50% of its total value.
RBA represents the ratio of the area under the curve of the formulation under consideration to the area under the curve of the IFN IR formulation.

All the formulations exhibit a sustained release profile accompanied by a fall in the $C_{max}$ with respect to the IR.

In comparison with comparative example 5, the terminal slope of all the formulations according to the present invention is lower, which indicates a sustained residual absorption.

For the formulations of example 2.1 and example 3 (10 mg/g PO-A1 and 30 mg/g PO-A2), sustained releases over more than 5 days (compared with approximately 3 days for the formulation of comparative example 5) respectively exhibiting RBA values of 57% and approximately 100% should be noted.

What is claimed is:

1. A liquid pharmaceutical formulation for the sustained release of at least one active principle (AP), said pharmaceutical formulation comprising at least one active principle (AP) and an aqueous suspension based on colloidal particles of a polymer (PO), or a pharmaceutically acceptable salt thereof, which satisfies the following four conditions:

(a) the polymer (PO) has the following formula (I):

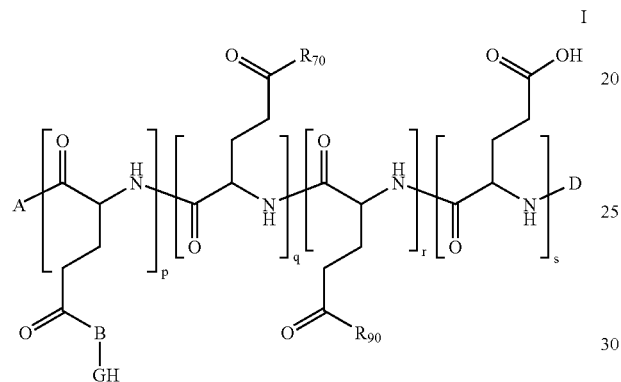

in which:
i) A independently is an —NHR group in which R represents H; a linear $C_2$ to $C_{10}$ or branched $C_3$ to $C_{10}$ alkyl or benzyl; a terminal amino acid residue or a terminal amino acid derivative of formula:

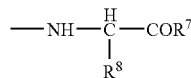

in which:
R$^7$ is selected from:
OH,
OR$^9$ wherein R$^9$ is a linear $C_2$ to $C_{10}$ or branched $C_3$ to $C_{10}$ alkyl or a benzyl or
NHR$^{10}$ wherein R$^{10}$ is an H, a linear $C_2$ to $C_{10}$ alkyl, a branched $C_3$ to $C_{10}$ alkyl or a benzyl;
R$^8$ is selected from an H, a linear $C_2$ to $C_{10}$ alkyl, a branched $C_3$ to $C_{10}$ alkyl or a benzyl;
ii) B is direct bond or a divalent, trivalent or tetravalent bonding group;
iii) D is selected from the group consisting of: H, a linear $C_2$ to $C_{10}$ acyl group, a branched $C_3$ to $C_{10}$ acyl group or a pyroglutamate;
iv) the hydrophobic groups GH each are, independently of one another, a group chosen from:
linear or branched $C_8$ to $C_{30}$ alkyls;
$C_8$ to $C_{30}$ alkylaryls or arylalkyls;
$C_8$ to $C_{30}$ (poly)cyclic compounds;
v) R$_{70}$ is a cationic group (CG) chosen from the group consisting of:
—NH—(CH$_2$)$_w$—NH$_3^+$ in which w is between 2 to 6 and,
—NH—(CH$_2$)$_4$—NH—C(=NH)—NH$_3^+$,
—O—(CH$_2$)$_2$—NH$_2^+$,
—O—(CH$_2$)$_2$—N+(CH$_2$)$_3$,
a group having the following formula:

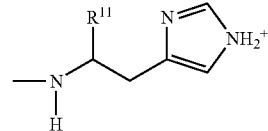

in which —R$^{11}$ is selected from the group consisting of —H, —CO$_2$H, an alkyl ester, —C(=O)—NH$_2$, —C(=O)—NH—CH$_3$ or —C(=O)—N(CH$_3$)$_2$;
an amino acid residue or an amino acid derivative of formula:

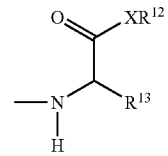

in which:
X is —O or —NH—,
R$^{12}$ is selected from the group consisting of: H, a linear $C_2$ to $C_{10}$ or branched $C_3$ to $C_{10}$ alkyl or a benzyl,
R$^{13}$ is —(CH$_2$)$_4$—NH$_3^+$, —(CH$_2$)$_3$NH—C(=NH)—NH$_3^+$, —(CH$_2$)$_3$NH$_3^+$;
vi) the counteranion of R$^{70}$ is an expedient group;
vii) R$_{90}$ is a hydroxyethylamino-, a hydroxyalkyloxy or a polyoxyalkylene;
viii) p, q, r and s are positive integers;
ix) (p)/(p+q+r+s) is defined as the molar degree of grafting of the hydrophobic groups GH and varies from 2 to 30 molar %, provided that each copolymer chain has, on average, at least three hydrophobic grafts;
x) (q)/(p+q+r+s) is defined as the molar degree of grafting of the cationic groups and varies from 10 to 98 molar %;
xi) (p+q+r+s) varies from 50 to 300;
xii) (r)/(p+q+r+s) varies from 0 to 78 molar %; and
xiii) (s)/(p+q+r+s) varies from 0 to 55 molar %
(b) the pHf value of the pH of said formulation is between 3.0 and 6.5;
(c) at the pHf value, the polymer (PO) forms a colloidal solution which associates spontaneously and noncovalently with the active principle (AP); and
(d) said formulation exhibits a precipitation factor PF of greater than 200.

2. The formulation of claim 1, wherein said formulation has a retention factor RQ of greater than 5.

3. The formulation of claim 1, wherein the polymer (PO) has a total degree of polymerization (DP) of between 50 and 300, wherein (s)/(p+q+r+s) varies from 0 to 45 molar %, (p)/(p+q+r+s) varies from 2 to 30 molar %, (q)/(p+q+r+s) varies from 40 to 98 molar % and (r)/(p+q+r+s) varies from 0 to 50 molar %.

4. The formulation of claim 1, wherein the polymer (PO) carries at least one graft of polyalkylene glycol bonded to a glutamate residue.

5. The formulation of claim 1, wherein the concentration of polymer (PO), or pharmaceutically acceptable salt thereof, in the formulation is between 4 and 50 mg/ml.

6. The formulation of claim 1, wherein the ratio R of the concentration of active principle (AP) to the concentration of polymer (PO), or pharmaceutically acceptable salt thereof, is between 0.0001 and 1.5.

7. The formulation of claim 1, further comprising $Zn^{++}$ divalent cations in a proportion of between 0.05 and 2 molar equivalents with respect to the molar concentration of cationic groups (CG).

8. The formulation of claim 1, wherein said formulation does not comprise added divalent cation.

9. The formulation of claim 1, wherein the active principle (AP) is selected from the group consisting of: proteins, glycoproteins, proteins bonded to one or more polyalkylene glycol chains, peptides, polysaccharides, liposaccharides, oligonucleotides, polynucleotides and mixtures thereof.

10. A solid pharmaceutical formulation for the sustained release of at least one active principle (AP), said formulation comprising a dry powder form obtained from a liquid formulation according to claim 1.

11. A process for the preparation of a formulation for the sustained release of at least one active principle (AP) according to claim 1, said process comprising the steps of:
1) preparing, at a pH value of between 3 and 6.5, an aqueous colloidal solution of a polyamino acid polymer (PO), said polyamino acid polymer (PO) has the following formula (I):

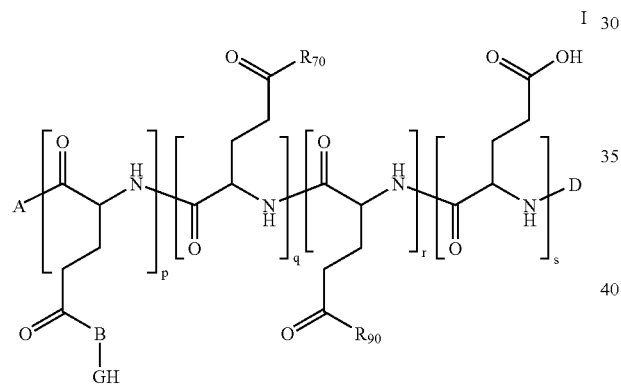

in which:
i) A independently is an —NHR group in which R represents H; a linear $C_2$ to $C_{10}$ or branched $C_3$ to $C_{10}$ alkyl or benzyl; a terminal amino acid residue or a terminal amino acid derivative of formula:

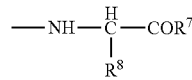

in which:
R$^7$ is selected from:
OH,
OR$^9$ wherein R$^9$ is a linear $C_2$ to $C_{10}$ or branched $C_3$ to $C_{10}$ alkyl or a benzyl or
NHR$^{10}$ wherein R$^{10}$ is an H, a linear $C_7$ to $C_{10}$ alkyl, a branched $C_3$ to $C_{10}$ alkyl or a benzyl;
R$^8$ is selected from an H, a linear $C_2$ to $C_{10}$ alkyl, a branched $C_3$ to $C_{10}$ alkyl or a benzyl;
ii) B is direct bond or a divalent, trivalent or tetravalent bonding group;

iii) D is selected from the group consisting of: H, a linear $C_2$ to $C_{10}$ acyl group, a branched $C_3$ to $C_{10}$ acyl group or a pyroglutamate;
iv) the hydrophobic groups GH each are, independently of one another, a group chosen from:
linear or branched $C_8$ to $C_{30}$ alkyls;
$C_8$ to $C_{30}$ alkylaryls or arylalkyls;
$C_8$ to $C_{30}$ (poly)cyclic compounds;
v) $R_{70}$ is a cationic group (CG) chosen from the group consisting of:
—NH—$(CH_2)_w$—$NH_3^+$ in which w is between 2 to 6 and,
—NH—$(CH_2)_4$—NH—C(=NH)—$NH_3^+$,
—O—$(CH_2)_2$—$NH_2^+$,
—O—$(CH_2)_2$—$N+(CH_3)_3$—,
a group having the following formula:

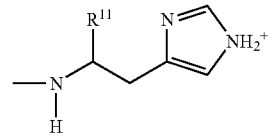

in which —R$^{11}$ is selected from the group consisting of —H, —$CO_2H$, an alkyl ester, —C(=O)—$NH_2$, —C(=O)—NH—$CH_3$ or —C(=O)—N$(CH_3)_2$;
an amino acid residue or an amino acid derivative of formula:

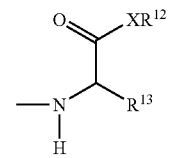

in which:
X is —O— or —NH—,
R$^{12}$ is selected from the group consisting of: H, a linear $C_2$ to $C_{10}$ or branched $C_3$ to $C_{10}$ alkyl or a benzyl,
R$^{13}$ is —$(CH_2)_4$—$NH_3^+$, —$(CH_2)_3$NH—C(=NH)—$NH_3^+$, —$(CH_2)_3NH_3^+$;
vi) the counteranion of R$^{70}$ is an expedient group;
vii) $R_{90}$ is a hydroxyethylamino-, a hydroxyalkyloxy or a polyoxyalkylene;
viii) p, q, r and s are positive integers;
ix) (p)/(p+q+r+s) is defined as the molar degree of grafting of the hydrophobic groups GH and varies from 2 to 30 molar %, provided that each copolymer chain has, on average, at least three hydrophobic grafts;
x) (q)/(p+q+r+s) is defined as the molar degree of grafting of the cationic groups and varies from 10 to 98 molar %;
xi) (p+q+r+s) varies from 50 to 300;
xii) (r)/(p+q+r+s) varies from 0 to 78 molar %; and
xiii) (s)/(p+q+r+s) varies from 0 to 55 molar %;
(b) the pHf value of the pH of said formulation is between 3.0 and 6.5
(c) at the pHf value, the polymer (PO) forms a colloidal solution which associates spontaneously and non-covalently with the active principle (AP); and
(d) said formulation exhibits a precipitation factor PF of greater than 200;
the respective molar fractions of cationic groups (CG) and hydrophobic groups (GH) and glutamate being such that 1 ml of said formulation precipitates during mixing with a volume of 1 ml of a test buffer solution Tp; and 2) adding at least one active principle (AP) to the polymer (PO) obtained in step 1, wherein said active principle associates noncovalently with the particles of the colloidal solution of said polymer.

12. The formulation of claim 1, wherein said formulation has a precipitation factor PF of greater than 800.

13. The formulation of claim 4, wherein the at least one graft is of polyethylene glycol.

14. The formulation of claim 1, wherein B is selected from the group of radicals consisting of: —O—, —NH—, —N($C_1$ to $C_5$ alkyl)-, residue of amino acid, of diol, of triol, of diamine, of triamine, of aminoalcohol and of hydroxy acid comprising from 1 to 6 carbon atoms.

* * * * *